(12) United States Patent
Jang et al.

(10) Patent No.: US 10,488,364 B2
(45) Date of Patent: Nov. 26, 2019

(54) THERMALLY STABLE AMMONIA GAS SENSOR USING ZNO-FUNCTIONALIZED ALGAN/GAN HETEROSTRUCTURE TRANSISTOR

(71) Applicant: University of Florida Research Foundation, Incorporated, Gainesville, FL (US)

(72) Inventors: Soohwan Jang, Gainesville, FL (US); Fan Ren, Gainesville, FL (US); Stephen J. Pearton, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 15/963,713

(22) Filed: Apr. 26, 2018

(65) Prior Publication Data
US 2018/0313785 A1    Nov. 1, 2018

Related U.S. Application Data

(60) Provisional application No. 62/491,507, filed on Apr. 28, 2017.

(51) Int. Cl.
*G01N 27/414* (2006.01)
*H01L 23/31* (2006.01)
(Continued)

(52) U.S. Cl.
CPC ..... *G01N 27/4146* (2013.01); *G01N 27/4141* (2013.01); *H01L 23/3171* (2013.01);
(Continued)

(58) Field of Classification Search
CPC ............ H01L 29/0665; H01L 29/0676; H01L 29/2003; H01L 29/205; H01L 29/413;
(Continued)

(56) References Cited

U.S. PATENT DOCUMENTS

| | | | | |
|---|---|---|---|---|
| 7,309,621 B2 * | 12/2007 | Conley, Jr. | ............. | B82Y 10/00 438/200 |
| 7,759,710 B1 * | 7/2010 | Chiu | .................... | A61B 5/1473 257/253 |

(Continued)

OTHER PUBLICATIONS

Hung et al. "Characteristics of carbon monoxide sensors made by polar and nonpolar zinc oxide nanowires gated AlGan/GaN high electron mobility transistor", Aug. 21, 2013, Applied Physics Letters 103, 083506 (2013) (Year: 2013).*

(Continued)

*Primary Examiner* — David C Spalla
(74) *Attorney, Agent, or Firm* — Alston & Bird LLP

(57) ABSTRACT

Methods and apparatuses for detecting ammonia are disclosed. A sensor can include a transistor having a gate, a drain, and a source. A layer of ammonia detecting material can be functionally attached to the transistor. The ammonia detecting material can be zinc oxide (ZnO) nanorods, which effectively functionalize the transistor by changing the amount of current that flows through the gate when a voltage is applied. Alternatively, or in addition to ZnO nanorods, films or nanostructure type metal oxides including TiO2, ITO, ZnO, $WO_3$ and AZO can be used. The transistor is preferably a high electron mobility transistor (HEMT).

18 Claims, 3 Drawing Sheets

(51) Int. Cl.

| | | |
|---|---|---|
| *H01L 29/08* | (2006.01) | |
| *H01L 29/20* | (2006.01) | |
| *H01L 29/205* | (2006.01) | |
| *H01L 29/423* | (2006.01) | |
| *H01L 29/45* | (2006.01) | |
| *H01L 29/47* | (2006.01) | |
| *H01L 29/778* | (2006.01) | |
| *G01N 33/00* | (2006.01) | |

(52) U.S. Cl.
CPC ...... *H01L 29/0891* (2013.01); *H01L 29/2003* (2013.01); *H01L 29/205* (2013.01); *H01L 29/42316* (2013.01); *H01L 29/452* (2013.01); *H01L 29/475* (2013.01); *H01L 29/7787* (2013.01); *G01N 33/0037* (2013.01); *G01N 33/0054* (2013.01)

(58) Field of Classification Search
CPC ............. H01L 29/423; H01L 29/42312; H01L 29/42316; H01L 29/452; H01L 29/475; H01L 29/7787; G01N 27/4141; G01N 27/4146; G01N 33/0037
See application file for complete search history.

(56) References Cited

U.S. PATENT DOCUMENTS

| | | | | |
|---|---|---|---|---|
| 2007/0210349 | A1* | 9/2007 | Lu ............................ | B82Y 5/00 257/252 |
| 2010/0188069 | A1* | 7/2010 | Ren .................. | G01N 33/54306 324/71.5 |
| 2012/0097917 | A1* | 4/2012 | Zhou ...................... | B82Y 15/00 257/12 |
| 2018/0128761 | A1* | 5/2018 | Kashyap ................ | G01N 27/02 |

OTHER PUBLICATIONS

Aslam et al., "A highly selective ammonia gas sensor using surface-ruthenated zinc oxide," Sensors and Actuators, May 1999, pp. 162-167, vol. 75.

Villalpando-Paez et al., "Fabrication of vapor and gas sensors using films of aligned $CN_x$ nanotubes," Chemical Physics Letters, Feb. 2004, pp. 137-143, vol. 386.

Jimenez et al., "Structural and gas-sensing properties of $WO_3$ nanocrystalline powders obtained by a sol-gel method from tungstic acid," IEEE Sensors Journal, Aug. 2002, pp. 329-335, vol. 2, No. 4.

Rigoni et al., "Environmental monitoring of low-ppb ammonia concentrations based on single-wall carbon nanotube chemiresistor gas sensors: detection limits, response dynamics, and moisture effects," Procedia Engineering, Sep. 2014, pp. 716-719, vol. 87.

Sama et al., "Site-selectively grown $SnO_2$ NWs networks on micromembranes for efficient ammonia sensing in humid conditions," Sensors and Actuators B: Chemical, Sep. 2016, pp. 402-409, vol. 232.

Tulliani et al., "Room temperature ammonia sensors based on zinc oxide and functionalized graphite and multi-walled carbon nanotubes," Sensors and Actuators B: Chemical, Mar. 2011, pp. 144-154, vol. 152.

Bannov et al., "Investigation of ammonia gas sensing properties of graphite oxide," Procedia Engineering, Sep. 2016, pp. 231-234, vol. 168.

Burgard et al., "Nitrogen dioxide, sulfur dioxide, and ammonia detector for remote sensing of vehicle emissions," Review of Scientific Instruments, Jan. 2006, pp. 1-5, vol. 77, No. 014101.

Rao et al., "Gas sensitivity of ZnO based thick film sensor to $NH_3$ at room temperature," Sensors and Actuators B, May 1999, pp. 166-169, vol. 55.

Jia et al., "Highly selective and sensitive phosphate anion sensors based on AlGaN/GaN high electron mobility transistors functionalized by ion imprinted polymer," Scientific Reports, Jun. 2016, pp. 1-7, vol. 6, No. 27728.

Hung et al., "Characteristics of carbon monoxide sensors made by polar and nonpolar zinc oxide nanowires gated AlGaN/GaN high electron mobility transistors," Applied Physics Letters, Aug. 2013, pp. 1-4, vol. 103, No. 083506.

Halfaya et al., "Investigation of the performance of HEMT-based NO, $NO_2$, and $NH_3$ exhaust gas sensors for automotive antipollution systems," Sensors, Feb. 2016, pp. 1-12, vol. 16, No. 273.

* cited by examiner

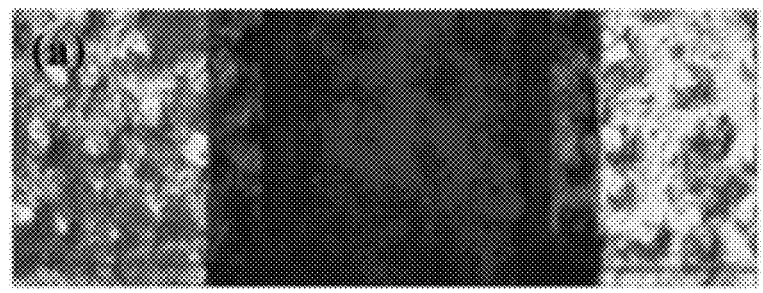
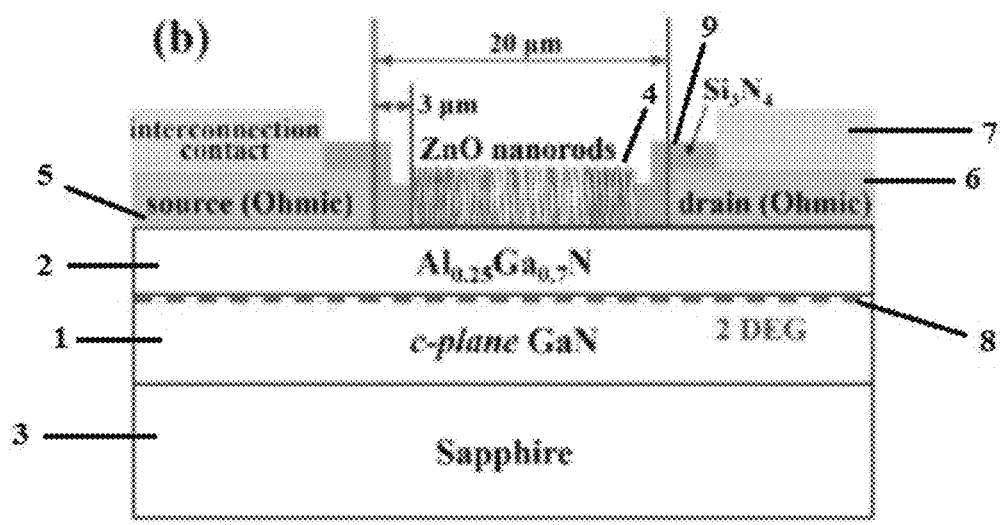
Figure 1(a)
Figure 1(b)
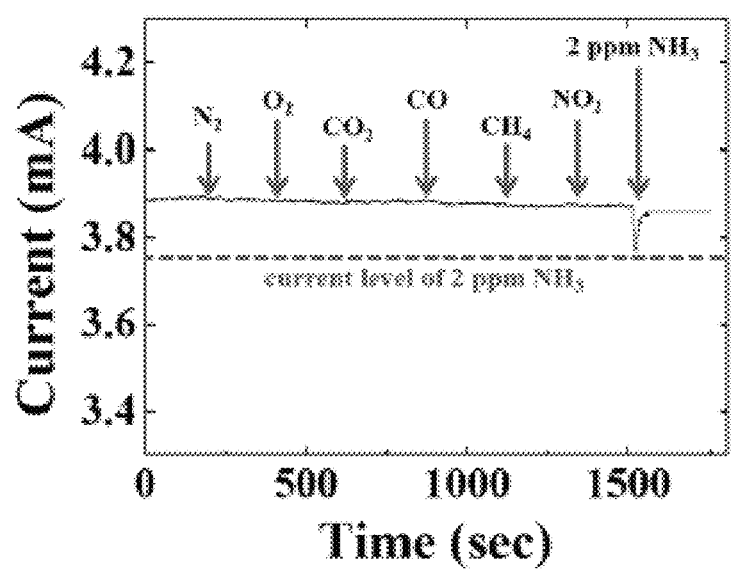
Figure 2

THERMALLY STABLE AMMONIA GAS SENSOR USING ZNO-FUNCTIONALIZED ALGAN/GAN HETEROSTRUCTURE TRANSISTOR

CROSS-REFERENCE TO RELATED APPLICATION

This application claims the benefit of U.S. Provisional Application Ser. No. 62/491,507, filed Apr. 28, 2017, which is incorporated herein by reference in its entirety, including any figures, tables, and drawings.

STATEMENT OF GOVERNMENT SUPPORT

This invention was made with government support under Grant No. HDTRA1-17-1-0011 awarded by the Department of Defense/Defense Threat Reduction Agency. The government has certain rights in the invention.

BACKGROUND

Detection of ammonia at low concentrations is necessary for monitoring environmental releases from refrigeration, agricultural (fertilizer and livestock) systems, and the automotive and chemical industries. Thus, there is a need for sensors that can measure concentrations of ammonia quickly, accurately, efficiently, and at a low cost.

BRIEF SUMMARY

Embodiments of the present invention include methods and apparatuses for detecting ammonia. Embodiments of the present invention also include methods for fabricating ammonia sensing apparatuses. Embodiments of the present invention include AlGaN/GaN high electron mobility transistors (HEMTs) with ZnO nanorod functionalized gates for ammonia sensing and concentration measurement.

The use of the HEMT platform allows for greater amplification than traditional transistors. Embodiments of the present invention can be utilized for monitoring environmental releases from refrigeration, agricultural (fertilizer and livestock) systems, and the automotive and chemical industries. Sensors of embodiments of the present invention may be particularly useful in detecting and measuring unreacted ammonia as part of the Selective Catalytic Reduction (SCR) process of reducing NOx emissions. Furthermore, sensors of embodiments of the present invention can exhibit high temperature stability, corrosion resistance, and chemical stability, especially relative to silicon based automotive exhaust gas sensors. The ZnO nanorods can be prepared with a sol-gel method, which is a low cost way to produce metal oxides.

In an embodiment, a sensor can include a transistor having a gate, a drain, and a source. A layer of ammonia detecting material can be functionally attached to the transistor as a gate to detect ammonia. The ammonia detecting material can be a layer of zinc oxide (ZnO) nanorods positioned on top of the gate of the transistor, effectively functionalizing the transistor to detect ammonia. Alternatively, or in addition to ZnO nanorods, films or nanostructure type metal oxides including $TiO_2$, ITO, ZnO, $WO_3$ and AZO can be used to functionalize the transistor. For example, the ZnO nanorods can function as a gate without a gate metal layer or the ZnO nanorods can be disposed on a gate metal layer (e.g., AlGaN layer-ZnO nanorods or AlGaN layer-gate (e.g., metal) layer-ZnO nanorods).

The transistor can be a high electron mobility transistor (HEMT). A first layer of gallium nitride (GaN) can be provided on a substrate as a base layer. A second layer of aluminum gallium nitride (AlGaN), a second layer, can be positioned above the first layer. The zinc oxide (ZnO) nanorods, or other functionalizing material, can be positioned above the layer of aluminum gallium nitride (AlGaN). Ammonia can be detected using the sensor by applying a voltage across the transistor's source and drain. When ammonia is present, the amount of current flowing through the transistor is reduced as atomic interactions between the functionalized layer and ammonia reduce the effective number of charge carriers. Once the sensor is moved to an ammonia free environment, the resistor returns back to normal operation, meaning the current flowing through the transistor increases and returns to its baseline. In some embodiments, the HEMT structure can include a GaN cap layer.

In another embodiment, a gas sensor can comprise: a gallium nitride (GaN) layer; an aluminum gallium nitride (AlGaN) layer disposed on the GaN layer; a source and a drain disposed on the AlGaN layer; and an ammonia adsorbing layer directly disposed on the AlGaN layer and placed between the source and the drain.

In yet another embodiment, a gas sensor can comprise: a substrate; a gallium nitride (GaN) layer disposed on the substrate; an aluminum gallium nitride (AlGaN) layer disposed on the GaN layer; a source and a drain disposed on the AlGaN layer; zinc oxide (ZnO) nanorods directly disposed on the AlGaN layer and placed between the source and the drain; a silicon nitride spacer placed between the source and the ZnO nanorods and between the drain and the ZnO nanorods; and a contact pad disposed on the source and the drain, wherein the source and the drain comprise a metal layer that forms an ohmic contact with the AlGaN layer.

BRIEF DESCRIPTION OF DRAWINGS

FIG. 1(a) shows a top-view optical microscope image of an experimental embodiment of the present invention.

FIG. 1(b) shows cross-sectional schematic diagram of a ZnO-functionalized AlGaN/GaN HEMT sensor according to an embodiment of the present invention.

FIG. 2 is a graph showing experimental results of a sensor according to the present invention receiving twenty (20) second sequential exposures of $O_2$ (100%), $CO_2$ (10%), CO (0.1%), $CH_4$ (4%), $NO_2$ (0.05%), and $NH_3$ (2 ppm) at 25° C. The drain-source voltage (VDS) was fixed at 4V.

DETAILED DESCRIPTION

Figure 3:
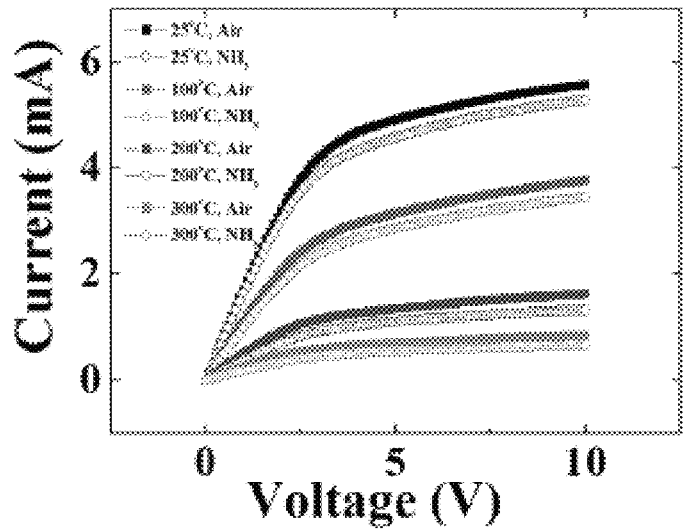
FIG. 3 is a graph showing HEMT sensor drain-source current characteristics measured in air or 2 ppm NH3 at 25, 100, 200, and 300° C.

Embodiments of the present invention include methods and apparatuses for detecting ammonia. Embodiments of the present invention also include methods for fabricating ammonia sensing apparatuses.

In an embodiment, an ammonia (and/or nitrogen and/or $N_xO_y$ (x and y can be, for example, integers; e.g., NO, $N_2O$, and/or $NO_2$)) detecting sensor can include a transistor having a gate, a drain 6, and a source 5. A layer of ammonia detecting material as the gate can be attached functionally to the transistor. The ammonia detecting material can be an exposed top layer of zinc oxide (ZnO) nanorods 4, which effectively functionalizes the transistor or sensing ammonia. Alternatively, or in addition to ZnO nanorods, films or nanostructure type metal oxides including $TiO_2$, ITO, ZnO, $WO_3$ and AZO can be applied.

The transistor is preferably a high electron mobility transistor (HEMT), which can operate in harsh environments including high temperatures. Advantageously, HEMT transistors can also provide high gain for precise measurements. As seen in FIG. 1, a gate can be formed in the area between the source 5 and the drain 6. The transistor can include first layer 1 of gallium nitride (GaN) and a second layer 2 of aluminum gallium nitride (AlGaN). The second layer 2 can be on the first layer 1. A layer of zinc oxide (ZnO) nanorods (or other functionalizing material) 4 can be provided on the layer of aluminum gallium nitride (AlGaN), or the second layer. When a voltage is applied to the source and drain of the transistor, a two-dimensional electron gas (2DEG) 8 can be created allowing current flow. Ammonia that is adsorbed to the functionalizing layer can affect the charge carriers of the two-dimensional electron 8, changing the current flow and allowing for concentration measurements.

A passivation layer (not shown) can be included between the transistor and the layer of zinc oxide (ZnO) nanorods. The passivation layer may be a thin layer of SiN. The functionalizing material 4 can be located between the source 5 and drain 6 of the transistor. The source 5, the drain 6, and the functionalizing material 4 are disposed on a source region, a drain region, and a gate region of the AlGaN layer, respectively. A spacer material 9 (e.g., SiN, or $Si_3N_4$) can be provided between the source 5 (or drain 6) and the layer of functionalizing material 4. A base or substrate layer 3 can be provided beneath the first layer 1, second layer 2, or both the first and second layers. Contact pads 7, the source 5, and the drain 6 can be made of metal materials, including one or more of titanium (Ti), aluminum (Al), nickel (Ni) and gold (Au). The substrate 3 can be made of sapphire, for example, and can have a crystal lattice structure that serves as the basis for forming the transistor structure. In some embodiments, the HEMT structure can include a GaN cap layer (not shown in the figures).

Transistors of embodiments of the present invention can take a variety of shapes and sizes depending on the performance and application requirements. For example, each spacer 9 of the spacer layer can be between 1 μm and 5 μm wide, inclusive. The layer of functionalizing material 4 can be from 10 μm to 50 μm wide. The sensor can measure ammonia concentrations ranging from 0.1 ppm to 2.0 ppm over temperatures ranging from 0 Celsius to 300 Celsius.

Sensors of embodiments of the present invention can provide concentration measurements that are highly resistant to, or selective against, interference from other gasses including oxygen, natural gasses, methane, carbon monoxide, carbon dioxide, and nitrous oxides. Sensors of the present invention can have quick response times (the time to realize 90% of saturated current), on the order of 1 second or less, with recovery times (the time to realize 10% of saturated current after removing ammonia/nitrogen/$N_xO_y$) that are less than 60 seconds.

Zinc Oxide (ZnO) nanorods can be grown using a hydrothermal method, which is a low cost, non-toxic, low temperature, and scalable process. The nanorods can be used as a sensing material to detect ammonia on the gate of an AlGaN/GaN high electron mobility transistor (HEMT). In addition to ZnO nanorods, films or nanostructure type metal oxides including $TiO_2$, ITO, $WO_3$ and AZO can be also used. Particularly, transparent ITO film can be easily adopted for commercial embodiments of the present invention due to its well-established deposition methods currently practiced in commercial LED manufacturing.

The subject invention includes, but is not limited to, the following exemplified embodiments.

Embodiment 1

A sensor (for detecting ammonia, nitrogen, and/or $N_xO_y$ (such as NO, $N_2O$, and/or $NO_2$)), the sensor comprising:
a transistor having a gate, a drain, and a source,
wherein the gate comprises a layer of ammonia detecting material attached functionally to a substrate of the transistor to detect ammonia (the ammonia detecting material can be zinc oxide (ZnO) nanorods attached to the transistor (functionalizing the transistor); alternatively, or in addition to ZnO nanorods, films or nanostructure type metal oxides including TiO2, ITO, ZnO, $WO_3$ and AZO can be used).

Embodiment 2

The sensor of Embodiment 1, wherein the transistor is a high electron mobility transistor (HEMT).

Embodiment 3

The sensor of any of Embodiments 1 to 2, wherein the HEMT includes a first layer of gallium nitride (GaN).

Embodiment 4

The sensor of any of Embodiments 1 to 3, wherein the HEMT includes a second layer of aluminum gallium nitride (AlGaN) (the second layer can be on the first layer).

Embodiment 5

The sensor of any of Embodiments 1 to 4, wherein the layer of zinc oxide (ZnO) nanorods is on the layer of aluminum gallium nitride (AlGaN), or the second layer.

Embodiment 6

The sensor of any of Embodiments 1 to 5, further comprising a passivation layer between the transistor and the layer of zinc oxide (ZnO) nanorods (the passivation layer may be a thin layer of SiN).

Embodiment 7

The sensor of any of Embodiments 1 to 6, wherein the layer of zinc oxide (ZnO) nanorods is between the source and the drain.

Embodiment 8

The sensor of any of Embodiments 1 to 7, wherein a spacer material (e.g., SiN, or $Si_3N_4$) is provided between the source and the layer of zinc oxide (ZnO) nanorods, or the drain and the layer of zinc oxide (ZnO) nanorods, or both.

Embodiment 9

The sensor of any of Embodiments 1 to 8, further comprising a passivation layer above the layer of zinc oxide (ZnO) nanorods.

Embodiment 10

The sensor of any of Embodiments 1 to 9, further comprising a substrate layer beneath the transistor (or beneath the GaN layer) (the substrate can be made of sapphire or silicon).

Embodiment 11

The sensor of any of Embodiments 1 to 10, wherein the HEMT includes a substrate layer beneath the GaN layer (the substrate can be made of sapphire or silicon).

Embodiment 12

The sensor of any of Embodiments 1 to 11, wherein each spacer of the spacer layer is between 1 μm and 5 μm wide.

Embodiment 13

The sensor of any of Embodiments 1 to 12, wherein the layer of zinc oxide (ZnO) nanorods is between 10 μm and 50 μm wide.

Embodiment 14

The sensor of any of Embodiments 1 to 13, wherein the sensor measures ammonia/nitrogen/$N_xO_y$ concentrations ranging from 0.1 ppm to 2.0 ppm.

Embodiment 15

The sensor of any of Embodiments 1 to 14, wherein the sensor measures ammonia/nitrogen/$N_xO_y$ concentrations temperatures from 0 Celsius to 300 Celsius (inclusive).

Embodiment 16

The sensor of any of Embodiments 1 to 14, wherein the sensor's measurements are resistant to (or selective against) other gasses (including oxygen, natural gasses, methane, carbon monoxide, carbon dioxide, and $NO_2$).

Embodiment 17

The sensor of any of Embodiments 1 to 14, further comprising contact pads attached to the source and/or drain comprising one or more of titanium (Ti), aluminum (Al), (Ni), and gold (Au) (the contact pads can be in layers of each metal; alternatively, the source and drain can be comprised of Ti/Al/Ni/Au).

Embodiment 18

The sensor of any of Embodiments 1 to 14, wherein the sensor's response time (the time to realize 90% of saturated current) is less than 1 second.

Embodiment 19

The sensor of any of Embodiments 1 to 14, wherein the sensor's recovery time (the time to realize 10% of saturated current after removing ammonia/nitrogen/$N_xO_y$) is less than 60 seconds.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

HEMT layer structures were grown on c-plane sapphire by Metal Organic Chemical Vapor Deposition (MOCVD). The layered structure included an initial 2 μm thick undoped GaN buffer followed by a 25 nm thick $Al_{0.25}Ga_{0.75}N$ layer. Sensor fabrication began with Ti/Al/Ni/Au (25/125/45/100 nm) metal deposition to form 50 μm×50 μm Ohmic contact pads separated by a gap of 20 μm with the standard lift-off of e-beam evaporated Ti/Al/Ni/Au-based metallization, and the samples were subsequently annealed at 850° C. for 45 seconds under a flowing $N_2$ ambient in a Heatpulse 610T system. Multiple energy and dose nitrogen ion implantation was used for device isolation and photoresist (AZ1045) was used as the mask to define the active region of the devices. Interconnection contacts were formed by lift-off of e-beam deposited Ti/Au (20/100 nm). A 250 nm thick plasma-enhanced chemical vapor deposited (PECVD) silicon nitride layer was used to passivate the source/drain regions. The gate and contact pad regions were defined using conventional photolithography and buffered oxide etchant for the subsequent ZnO nanorod growth on the AlGaN surface and electrical probing of the devices. As a result, the ZnO nanorods can be in direct physical contact with the AlGaN surface and can also exposed be to the outside.

The gate area of the sensors was functionalized with ZnO nanorods for $NH_3$ sensing. The ZnO nanorod growth started with ZnO nano-crystal seed preparation. A ZnO nano-crystal seed solution was mixed by slowly adding 30 mM NaOH (Sigma-Aldrich) in methanol to a 10 mM zinc acetate dihydrate (Zn(O2CCH3)2.2H2O, Sigma-Aldrich) solution at 60° C. over a 2 hour period. The ZnO nano-crystal seed solution was spun on the HEMT, and then the sample was heated on a hot plate at 300° C. for 30 minutes in an air ambient. The nano-crystalline seed coated sensor chips were then immersed in an aqueous mixture of 20 mM zinc nitrate hexahydrate (Zn(NO3)2.6H2O, Sigma-Aldrich) and 20 mM hexamethylenetetramine (C6H12N4, Sigma-Aldrich) and put in the oven at ~94° C. for 3 hours for the ZnO nanorod growth. After the nanorod growth, the device was removed from the solution, thoroughly rinsed with de-ionized water to remove any residual salts, and dried with nitrogen gas. Photoresist was used to pattern the gate area and dilute 1 HCl:10 $H_2O$ solution was used to etch off the ZnO nanorods around the gate and contact pad area. An optical microscope image and schematic structure of the fabricated ZnO-functionalized AlGaN/GaN HEMT sensor is shown in FIG. 1.

The completed ZnO nanorods were exposed to controlled concentrations of NH3 balanced with synthetic air in a test chamber in which mass flow controllers controlled the gas flow rate and injection time. The sensors were mounted on a probe stage in the chamber with electrical feed-throughs connected to an HP4155C parameter analyzer. The devices were exposed to NH3 concentrations of 0.1-2 ppm at temperatures from 25 to 300° C.

FIG. 2 shows that the sensors were completely selective at 25° C. for 2 ppm NH3 over $O_2$ (100%), $CO_2$ (10%), CO (0.1%), $CH_4$ (4%), and $NO_2$ (0.05%) under the same detection conditions as used for the $NH_3$. The exposure time for each of these gases was twenty (20) second and the source-drain voltage on the HEMT was held constant at 4.0V.

FIG. 3 shows the drain current-voltage (I-V) characteristics of the HEMT sensor at four different temperatures (25, 100, 200 and 300° C.) in either air or 2 ppm $NH_3$. Note that the drain current decreases in all cases, which is the opposite to what is observed with detection of reducing gases with HEMT sensors. In that case, the detection mechanism involves an increase in positive charge at the heterointerface that creates the two-dimensional electron gas (2DEG) used as the transistor channel. For example, a hydrogen sensor employs a catalytic Schottky gate metal, platinum, in the gate region. The 2DEG channel is very sensitive to changes in AlGaN surface charge. When a Schottky HEMT of this type is exposed to hydrogen gas, hydrogen molecules are adsorbed on the active sites of the platinum before being decomposed into atoms. Then, the dissociated hydrogen atoms diffuse into the AlGaN interface to form effective positive gate surface charges, thereby decreasing the effective barrier height and increasing drain current. In effect, the drain current response to hydrogen is amplified through the 2DEG of AlGaN/GaN heterostructure.

In the present case of $NH_3$ detection, the 2DEG current decreases upon exposure to the gas, suggesting that there is an increase in negative charge at the heterointerface. The mechanism of ammonia reacting with the ZnO nanorods may involve adsorption of oxygen that is reduced by electrons in the n-type ZnO, leading to the reaction $2NH_3 + 3O\text{-ads} \leftrightarrow 3H_2O + N_2 + 3e-$. The ZnO nanorods always exhibit n-type conductivity related to oxygen vacancies, and therefore can significantly enhance oxygen molecular adsorption. The oxygen species react with the ammonia to return more electrons to the ZnO surface, resulting in an abrupt change in the conductivity of the sensor and enhancing the gas-sensing properties of the nanorod-functionalized HEMT.

Figure 4A:
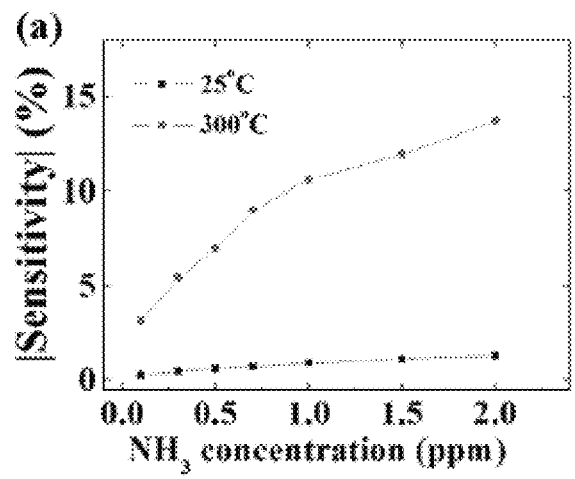
FIG. 4(a) shows absolute sensitivity of sensors as a function of NH3 concentration for either 25 or 300° C. with a drain-source voltage (VDS) of 1 V.
Figure 4B:
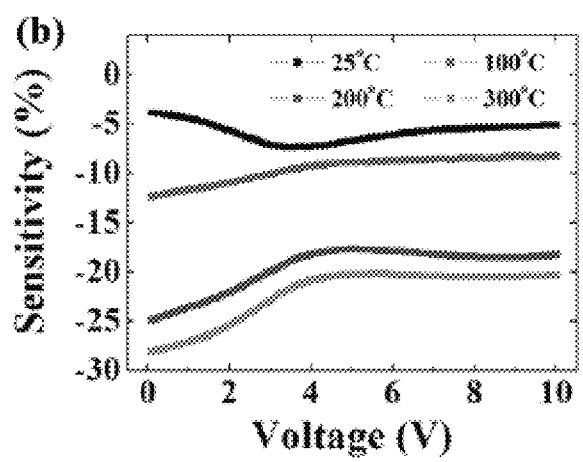
FIG. 4(b) is a graph of sensitivity as a function of VDS at four different temperatures (25, 100, 200 or 300° C.) for continuous 2 ppm $NH_3$ exposure.

The sensitivity of the sensors is defined as $(I_{NH3} - I_{Air})/I_{Air} \times 100\%$, where $I_{NH3}$ is the current under the various concentrations of ammonia and $I_{Air}$ is the current under an air ambient. As shown in FIG. 4(a), the absolute detection sensitivity increased monotonically with ammonia concentration at all temperatures, from 0.28% (25° C.) and 3.17% (300° C.) for 0.1 ppm to 1.32% (25° C.) and 13.73% (300° C.) for 2 ppm with a drain-source voltage of 1.0V. The latter condition is attractive for reduced power consumption and is in the linear region of the HEMT I-V plot. The sensitivity was also a function of applied voltage and was generally higher at lower biases where the HEMT shows linear I-V characteristics (FIG. 3), as shown in FIG. 4(b). Thus, the HEMT provides a wide voltage operation range and the choice of bias can be made based on power consumption requirements.

Figure 5:
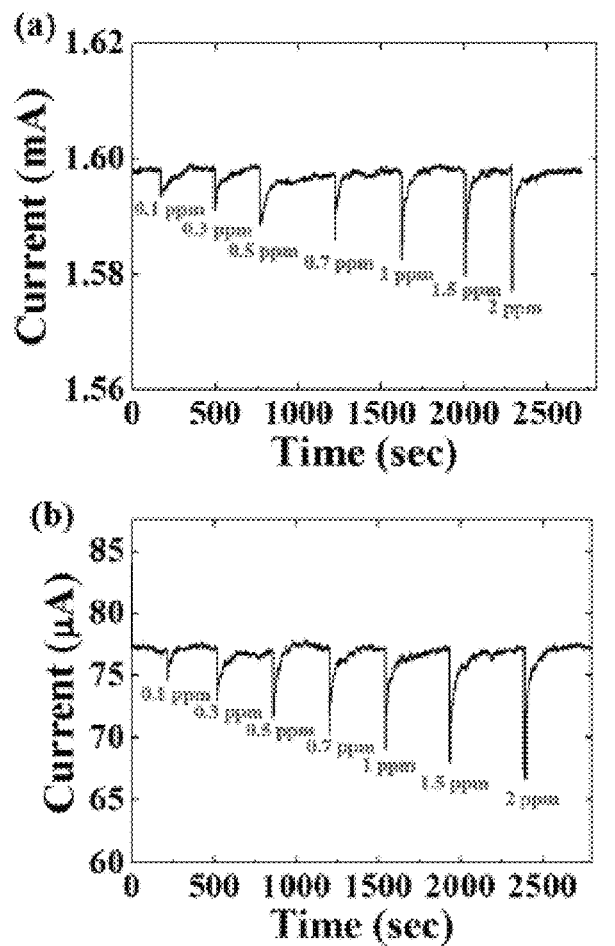
FIG. 5 shows the time response of sensors to 5 second exposures of 0.1-2 ppm $NH_3$, followed in by a return to ammonia-free air with VDS of 1 V at (a) 25 and (b) 300° C.

The response and recovery characteristics of sensors are important for achieving precise control of anti-pollution systems. Response time is defined as the time required to reach 90% of saturated current after 2 ppm ammonia exposure, and recovery time is defined as the time required to reach 10% of the saturated current after reintroducing ammonia-free air. Response times for all concentrations of ammonia exposures were one (1) second, which was the unit measurement time for both 25 and 300° C., as shown in FIG. 5. The recovery times were faster at higher temperatures. The recovery times for 2.0 ppm ammonia were 53 and 40 seconds for 25 and 300° C., respectively.

Figure 6:
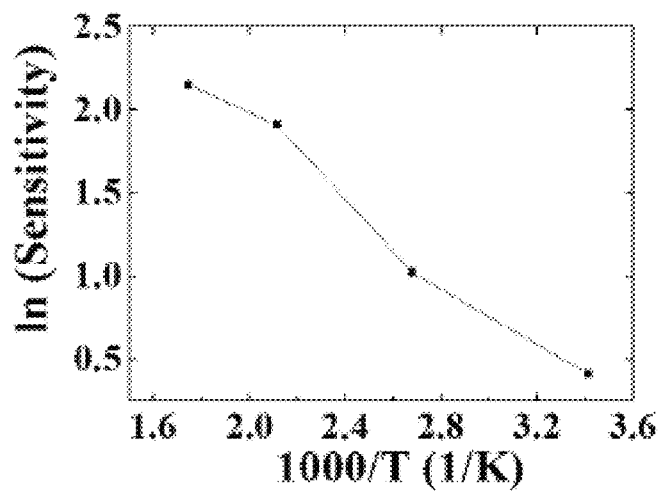
FIG. 6 shows an Arrhenius plot of sensitivity to detection of 2 ppm $NH_3$.

FIG. 6 shows an Arrhenius plot of sensitivity, leading to an activation energy of 0.09 eV for ammonia sensing with the ZnO nanorod-functionalized HEMT. This is the energy of the rate-limiting step in the formation of a charge depletion layer on the surface of the ZnO due to electron trapping on adsorbed oxygen species and the transfer of the negative charge to the AlGaN surface from the reaction previously discussed.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. C. S. Rout, M. Hegde, A. Govindaraj, and C. N. R. Rao, Nanotechnology, 18, 205504 (2007).
2. B. Timmer, W. Olthuis, and A. Berg, Sens. Actuators, B, 107, 666 (2005).
3. M. Aslam, V. A. Chaudhary, I. S. Mulla, S. R. Sainkar, A. B. Mandale, A. A. Belhekar, and K. Vijayamohanan, Sens. Actuators, A. 75, 162 (1999).
4. M. S. Wagh, G. H. Jain, D. R. Patil, S. A. Patil, and L. A. Patil, Sens. Actuators, B, 115, 128 (2006).
5. Y. Wang, X. Wu, Q. Su, Y. Li, and Z. Zhou, Solid-State Electron., 45, 347 (2001).
6. P. Guo, and H. Pan, Sens. Actuators, B, 114, 762 (2006).
7. E. Bekyarova, M. Davis, T. Burch, M. E. Itkis, B. Zhao, S. Sushine, and R. C. Haddon, J. Phys. Chem. B, 108, 19717 (2004).
8. N. H. Quang, M. V. Trinh, B. Lee, and J. Huh. Sens. Actuators, B, 113, 341 (2006).
9. F. V. Paez, A. H. Romero, E. M. Sandoval, L. M. Martinez, H. Terrones, and M. Terrones, Chem. Phys. Lett., 386, 137 (2004).
10. C. S. Rout, S. H. Krishna, S. R. C. Vivekchand, A. Govindaraj, and C. N. R. Rao, Chem. Phys. Lett., 418, 586 (2006).
11. C. S. Rout, A. Govindaraj, and C. N. R. Rao, J. Mater. Chem., 16, 3936 (2006).
12. I. Jimenez, J. Arbiol, A. Cornet, and J. R. Morante, IEEE Sens. J., 2, 329 (2002).
13. B. Marquis, and J. Vetelino, Sens. Actuators, B, 77, 100 (2001).
14. D. Zhang, C. Jiang, and Y. Sun, J. Alloys Compd., 698, 476 (2017).
15. S. Han, X. Zhuang, Y. Jiang, X. Yang, L. Li, and J. Yu, Sens. Actuators, B, 243, 1248 (2017).
16. F. Rigoni, S. Tognolini, P. Borghetti, G. Drera, S. Pagliara, A. Goldoni, and L. Sangaletti, Procedia Eng., 87, 716 (2014).
17. R. H. Vignesh, K. V. Sankar, S. Amaresh, Y. S. Lee, and R. K. Selvan, Sens. Actuators, B, 220, 50 (2015).
18. J. Samà, S. Barth, G. Domènech-Gil, J. D. Prades, N. López, O. Casals, I. Gràcia, C. Cané, and A. Romano-Rodríguez, Sens. Actuators, B, 232, 402-409 (2016).

19. J. M. Tulliani, A. Cavalieri, S. Musso, E. Sardella, and F. Geobaldo, Sens. Actuators, B, 152, 144 (2011).
20. A. G. Bannov, J. Prágek, O. Jašek, A. A. Shibaev, and L. Zajíčková, Procedia Eng., 168, 231 (2016).
21. B. Chatterjee, and A. Bandyopadhyay, Environ. Qual. Manage., 26, 89 (2016).
22. M. Gautam, and A. H. Jayatissa, J. Appl. Phys., 111, 094317 (2012).
23. D. A. Burgard, T. R. Dalton, G. A. Bishop, J. R. Starkey, and D. H. Stedman, Rev. Sci. Instrum., 77, 014101 (2006).
24. V. B. Raj, A. T. Nimal, Y. Patinar, M. U. Sharma, and V. Gupta, Sens. Actuators, B, 166, 576 (2012).
25. G. S. T. Rao, and D. T. Rao, Sens. Actuators, B, 55, 166 (1999).
26. Y. L. Tang, Z. J. Li, J. Y. Ma, Y. J. Guo, Y. Q. Fu, and X. T. Zu, Sens. Actuators, B, 201, 114 (2014).
27. X. Wang, J. Zhang, and Z. Zhu, Appl. Surf. Sci., 252, 2404 (2006).
28. X. Jia, D. Chen, L. Bin, H. Lu, R. Zhang, and Y. Zheng, Sci. Rep., 6, 27728 (2015).
29. S. C. Hung, W. Y. Woon, F. Ren, and S. J. Pearton, Appl. Phys. Lett. 103, 083506 (2013).
30. C. F. Lo, Y. Xi, L. Liu, S. J. Pearton, S. Dore, C. H. Hsu, A. M. Dabiran, P. P. Chow, and F. Ren, Sens. Actuators, B, 176, 708 (2013).
31. B. S. Kang, H. T. Wang, F. Ren, and S. J. Pearton, J. Appl. Phys. 104, 031101 (2008).
32. B. H. Chu, B. S. Kang, F. Ren, C. Y. Chang, Y. L. Wang, S. J. Pearton, A. V. Glushakov, D. M. Dennis, J. W. Johnson, P. Rajagopal, J. C. Roberts, E. L. Piner, and K. J. Linthicum, Appl. Phys. Lett., 93, 042114 (2008).
33. Y. Halfaya, C. Bishop, A. Soltani, S. Sundaram, V. Aubry, P. L. Voss, J. P. Salvestrini, and A. Ougazzaden, Sensors 16, 273 (2016).
34. H. I. Chen, Y. J. Liu, C. C. Huang, C. S. Hsu, C. F. Chang, and W. C. Liu, Sens. Actuators, B, 155, 347 (2011).
35. H. I. Chen, C. S. Hsu, C. C. Huang, C. F. Chang, P. C. Chou, and W. C. Liu, IEEE Electron Device Lett., 33, 612 (2012).
36. S. Jang, J. Kim, and K. H. Baik, J. Electrochem. Soc., 163, B456 (2016).
37. K. H. Baik, J. Kim, and S. Jang, ECS Trans., 72, 23 (2016).
38. S. Jang, P. Son, J. Kim, S. Lee, and K. H. Baik, Sens. Actuators, B, 222, 43 (2016).

What is claimed is:

1. A sensor for detecting at least one of ammonia and $N_xO_y$, the sensor comprising: a transistor having a gate, a drain, and a source,
wherein the gate comprises a layer of ammonia-detecting material attached functionally to a substrate of the transistor,
wherein the ammonia detecting material comprises zinc oxide (ZnO) attached to the transistor, thereby effectively functionalizing the transistor, and at least a portion of a surface of the ZnO is exposed to an external environment to detect ammonia.

2. The sensor according to claim 1, wherein the ammonia detecting material comprises films or nanostructure type metal oxides including one or more of $TiO_2$, ITO, ZnO, $WO_3$ and AZO.

3. The sensor according to claim 1, wherein the transistor is a high electron mobility transistor (HEMT).

4. The sensor according to claim 3, wherein the HEMT includes a first layer of gallium nitride (GaN).

5. The sensor according to claim 4, wherein the HEMT includes a second layer of aluminum gallium nitride (AlGaN) on the first layer.

6. The sensor according to claim 1, further comprising a passivation layer between the transistor and the ammonia detecting material.

7. The sensor of according to claim 1, wherein the ammonia detecting material is a layer of zinc oxide (ZnO) nanorods between the source and drain of the transistor.

8. A gas sensor, comprising:
a gallium nitride (GaN) layer;
an aluminum gallium nitride (AlGaN) layer disposed on the GaN layer;
a source and a drain disposed on the AlGaN layer; and
an ammonia adsorbing layer directly disposed on the AlGaN layer and placed between
the source and the drain,
wherein the ammonia adsorbing layer comprises zinc oxide (ZnO) and wherein at least a portion of a surface of the ZnO is exposed to an external environment to detect ammonia.

9. The gas sensor according to claim 8, wherein the ammonia adsorbing layer further comprises at least one of titanium dioxide ($TiO_2$), indium tin oxide (ITO), tungsten trioxide ($WO_3$), and aluminum-doped zinc oxide (AZO).

10. The gas sensor according to claim 8, further comprising a spacer placed between the source and the ammonia adsorbing layer and between the drain and the ammonia adsorbing layer.

11. The gas sensor according to claim 10, wherein the spacer comprises a silicon nitride layer.

12. The gas sensor according to claim 10, wherein the source and the drain comprises a metal layer including at least one of titanium (Ti), aluminum (Al), nickel (Ni), and gold (Au), and the metal layer forms an ohmic contact with the AlGaN layer.

13. The gas sensor according to claim 12, further comprising a contact pad disposed on the source and the drain.

14. The gas sensor according to claim 13, wherein the spacer is in contact with side surfaces of the source and the drain, and in contact with top surfaces of the source and the drain.

15. The gas sensor according to claim 13, wherein the GaN layer is a c-plane GaN layer.

16. The gas sensor according to claim 13, further comprising a two-dimensional electron gas (2DEG) channel between the GaN layer and the AlGaN layer.

17. The gas sensor according to claim 16, further comprising a Sapphire substrate disposed below the GaN layer.

18. A gas sensor, comprising:
a substrate;
a gallium nitride (GaN) layer disposed on the substrate;
an aluminum gallium nitride (AlGaN) layer disposed on the GaN layer;
a source and a drain disposed on the AlGaN layer;
zinc oxide (ZnO) nanorods directly disposed on the AlGaN layer and placed between the source and the drain;
a silicon nitride spacer placed between the source and the ZnO nanorods and between the drain and the ZnO nanorods; and
a contact pad disposed on the source and the drain,
wherein the source and the drain comprise a metal layer that forms an ohmic contact with the AlGaN layer, wherein at least a portion of a surface of the ZnO nanorods is exposed to an external environment to detect ammonia.

\* \* \* \* \*